United States Patent [19]

Mawhinney

[11] Patent Number: 4,991,585

[45] Date of Patent: Feb. 12, 1991

[54] NON-INVASIVE RESPIRATION AND/OR HEARTBEAT MONITOR OR THE LIKE

[75] Inventor: Daniel D. Mawhinney, Livingston, N.J.

[73] Assignee: MMTC, Inc., Princeton, N.J.

[21] Appl. No.: 492,959

[22] Filed: Mar. 13, 1990

[51] Int. Cl.$^5$ ............................ A61B 5/00; A61B 5/08
[52] U.S. Cl. ........................ 128/653 R; 343/700 MS; 128/721; 340/573
[58] Field of Search ................. 128/653 R, 671, 716, 128/721, 782; 343/700 MS File, 893, 894; 324/632, 642, 644, 645; 340/573

[56] References Cited

U.S. PATENT DOCUMENTS

| | | | |
|---|---|---|---|
| 3,483,860 | 12/1969 | Namcrow | 128/653 |
| 3,562,642 | 2/1971 | Hochschild | 324/644 |
| 3,796,208 | 3/1974 | Bloice | 128/782 |
| 4,738,264 | 4/1988 | Orlando | 128/721 |
| 4,853,692 | 8/1989 | Wolk et al. | 340/573 |
| 4,926,868 | 5/1990 | Larsen | 128/695 |

OTHER PUBLICATIONS

Barr, "At Home With a Monitor", 1979.
Haight et al., "A Manual for Home Monitoring", 1982.

*Primary Examiner*—Kyle L. Howell
*Assistant Examiner*—K. M. Pfaffle
*Attorney, Agent, or Firm*—George J. Seligsohn

[57] ABSTRACT

A microwave carrier signal is transmitted into certain tissue (such as the thorax) of a patient from an outer one of three linearly-arranged independent elements of an antenna assembly. Back-scatter portions of the carrier signal are received by both the middle and the other outer ones of the elements of the antenna assembly. The back-scatter portion received by the middle element is phase-modulated by a modulation frequency and re-transmitted into the tissue of the patient, and the other outer element also receives a back-scatter portion of this retransmitted phase-modulated signal. The total signal received by this other outer element is beat against the original microwave signal in a mixer and the output of the mixer is applied as an input to a bandpass filter, which passes only the phase-modulated signal. The envelope of the bandpass filter output is indicative of motion (e.g., breathing rate) of the patient.

The detection of spurious motions of objects located outside of the target area of interest of the patient is minimized in the disclosed monitor.

11 Claims, 2 Drawing Sheets

NON-INVASIVE RESPIRATION AND/OR HEARTBEAT MONITOR OR THE LIKE

The government has rights in this invention pursuant to Grant No. SSS-1 (M)--1R43-HL-42184-01 awarded by the Department of Health and Human Services.

BACKGROUND OF THE INVENTION

Various types of respiration and heartbeat monitors are known in the art for monitoring cyclic movement within the thorax of an individual, such as a post-operative patient or an infant subject to sudden crib death, for the purpose of actuating an alarm in case of trouble. Among these is one that is disclosed in the copending U.S. patent application Ser. No. 07/190,177, filed May 4, 1988 by Fred Sterzer, and assigned to the same assignee as the present invention. As disclosed in this patent application, one module is situated adjacent the chest and another module is situated adjacent the back of a post-operative patient. A carrier signal, which may have a frequency of 40 Mhz, is transmitted from a first of these modules through the thorax of a patient to second of these modules. At the second module, the carrier signal is modulated by a given modulation frequency and then retransmitted back to the first module. At the first module, the retransmitted signal is homodyned with the carrier frequency in a frequency converter that provides a filtered output that rejects the frequency-converted baseband, but passes the frequency-converter modulation frequency. Both the frequency-converted baseband and modulation frequency will be doppler-shifted in accordance with cardiopulmonary movements within the thorax. However, spurious doppler frequency shifts due to back-scatter of the originally transmitted carrier signal from moving objects not within the thorax of the patient (i.e. carrier-signal leakage that has never been modulated by the modulation frequency) occurs only in the rejected frequency-converted basdband. Such a non-invasive monitor minimizes the undesired occurrence of false alarms, while providing a high signal-to-noise cyclic cardiopulmonary waveform for analysis, thereby permitting accurate determination of whether or not an abnormal condition exists that requires the actuation of an alarm.

SUMMARY OF THE INVENTION

The present invention, which, in an illustrative embodiment, employs only a single module adjacent the thorax of a patient, is particularly directed to an alternative to the non-invasive monitor disclosed in the aforesaid patent application. The alternative monitor of the present invention makes use of the interferometric effects on a phase-modulated carrier signal caused by movement within certain tissue of an individual, such as the thorax of the patient, rather than a doppler shift in the frequency thereof, to substantially eliminate carrier-signal leakage and thereby provide a high signal-to-noise cyclic cardiopulmonary waveform for analysis to permit accurate determination of whether or not an abnormal condition exists that requires the actuation of an alarm.

More generally, the present invention is directed to apparatus which comprises a radiator (e.g., an antenna) including three independent elements, with separate ones of the three independent radiator elements being respectively coupled to first means, second means and mixer means. The first means, which includes a source of original carrier signal having a given frequency and phase coupled to a first of the three independent radiator elements, transmits the original carrier signal into an object, which may be certain tissue (e.g., thorax) of an individual, whereby some of the transmitted carrier signal is back-scattered and a respective back-scattered portion is received by each of a second and a third of the three independent radiator elements. The second means, which includes a source of modulation signal having a second frequency and a phase shifter coupled to the second of the three independent radiator elements, phase modulates the back-scattered portion received by the second of the three independent radiator elements in accordance with the modulation signal and retransmits therefrom the phase-modulated portion back into the object, whereby some of the retransmitted phase-modulated portion is back-scattered and received by the third of the three independent radiator elements. The mixer means, coupled to the third of the three independent radiator elements and to the source of original carrier signal, beats both of the back-scattered portions received by the third of the three independent radiator elements against the original carrier signal, whereby the mixer means has an output which includes a component having the second frequency. The apparatus further comprises third means, which includes bandpass filter means having the mixer-means output applied as an input thereto, for passing the mixer-means output component having the second frequency and rejecting all other components of the mixer-means output, whereby the bandpass filter means derives an output signal having an envelope indicative of movement within the object.

DESCRIPTION OF THE PREFERRED EMBODIMENT

Figure 1:
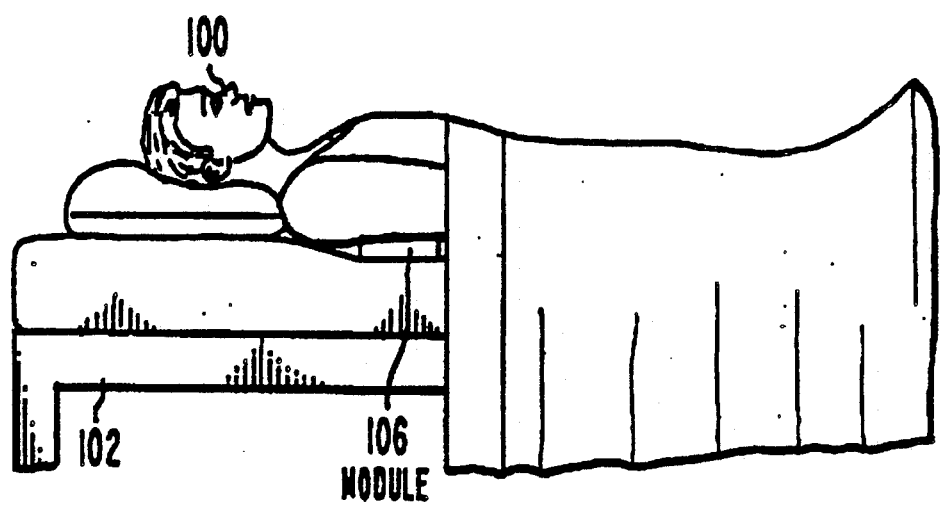
FIG. 1 is an illustrative showing of a patient lying on a bed in a post-operative recovery room, intensive-care unit, coronary-care unit or the like, with a single battery-energized module adjacent to his back.

Referring to FIG. 1, there is shown a patient 100 lying on his back in bed 102. Positioned between the top of the mattress of bed 102 and the back of patient 100 in cooperative spatial relationship with the thorax of patient 100 is a suitably-padded single battery-energized module 106, which includes circuitry for transmitting a low-power carrier signal, preferably at a microwave frequency, receiving back-scatter from objects both inside and outside of the patient's body that are significantly irradiated by the transmitted carrier signal, and then processing the received back-scatter. Due to a high degree of absorption by body tissue, microwave power from module 106 irradiating the thorax of patient 100 penetrates the thickness of the thorax tissue only to a limited extent. Thus, the positioning of module 106 shown in FIG. 1 causes the body tissue of patient 100 to act as a shield that prevents objects located outside of the body of patient 100 from being significantly irradiated from module 106 by transmitted carrier signal which passes entirely through his body tissue. Nevertheless, some small but still significant fraction of transmitted carrier signal from module 106 does take place around the body of patient 100 and irradiates both moving and non-moving objects outside of the body of patient 100. Although module 106 receives back-scatter from both irradiated objects outside of the body of patient 100 and from irradiated thorax tissue, it is essential that the processing of received back-scatter discriminates to a high degree against back-scatter from irradiated objects outside of the body of patient 100 in order to derive an accurate and relaibel alarm-control output signal. The circuitry shown in FIG. 2, in accordance with the principles of the present invention, provides this high degree of discrimination.

Figure 2:
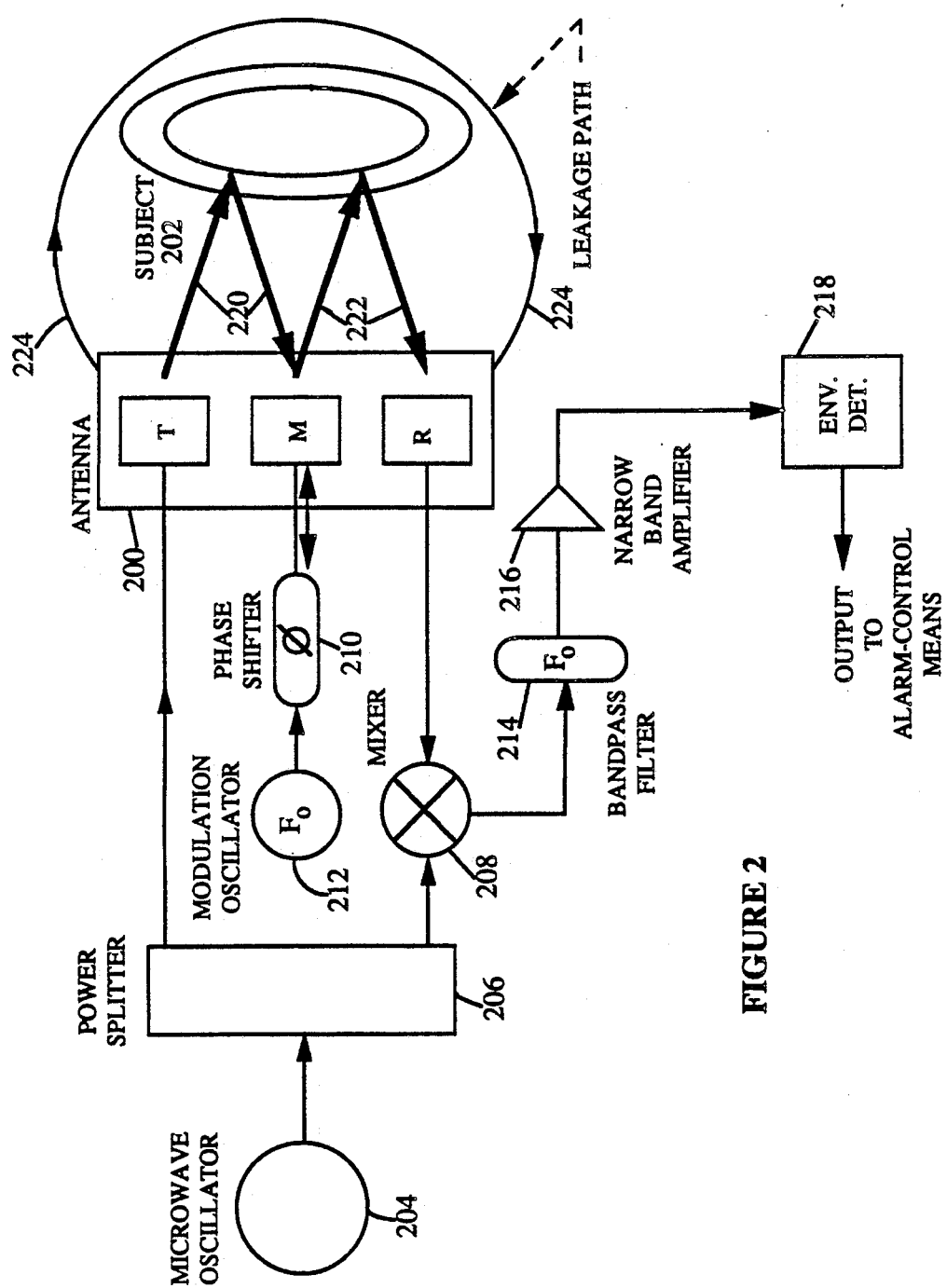
FIG. 2 is a block diagram of apparatus embodying the present invention, at least a portion of which apparatus may be housed in the module shown in FIG. 1.

Referring to FIG. 2, there is shown antenna 200 located adjacent subject 202 (which subject 202 is assumed to be that area on the back of the thorax of patient 100 which is defined by the interface of the radiation field pattern of antenna 200 thereon). Antenna 200, which may be a flat microstrip antenna, is comprised of three independent elements T, M and R, which preferably are linearly-arranged with element M being disposed in between elements T and R, as shown in FIG. 2.

A carrier signal from an unmodulated continuous-wave (cw) microwave oscillator 204 a first frequency and a given phase is split into two parts by power splitter 206. One of the two carrier-signal parts is applied to element T of antenna 200 and the other of the two carrier-signal parts is applied as a first input to mixer 208. Any signal received by element R of antenna 200 is applied as a second input to mixer 208. Any signal received by element M of antenna 200 is applied to phase shifter 210, where it is shifted in phase by an amount determined by phase shifter 210 and then applied back to element M of antenna 200.

More specifically, phase shifter 210, which operates as a phase modulator, may be alternatively comprised of either a switched open/shot circuit reactance or a varactor (variable-capacitance diode), either one of which is controlled in accordance with a modulation signal having a second frequency $F_o$ applied to phase shifter 210 from modulation oscillator 212. The second frequency $F_o$ may have a specific fixed value or, alternatively, a coded sequence of values. In any case, the phase modulation provided by phase shifter 210 causes the particular phase of the signal received by element M of antenna 200 to dither (i.e., shift back and forth) at second frequency $F_o$ about this particular phase by a phase displacement determined by the amplitude of the modulation signal.

The output from mixer 208, which includes all beat-frequency components derived from beating the signal applied to its second input from antenna element R against the carrier signal applied to its first input from power splitter 206, is applied as an input to bandpass filter 214 which passes only a beat-frequency component substantially equal in value to the second frequency $F_o$ and rejects all other beat-frequency components. Assuming second frequency $F_o$ to be a specific fixed frequency, the output from bandpass filter 214 is amplified by narrow-band amplifier 216 and applied as an input to envelope detector 218. Should the value of second frequency $F_o$ be varied in accordance with a coded sequence, the pass band of bandpass filter 214 and/or narrow-band amplifier 216 would need to be altered in accordance with such coded sequence. For instance, the pass band of filter 214 could be sufficiently wide to accommodate all values of second frequency $F_o$ in the coded sequence, with a separate normally-disabled narrow-band for amplifier 216 being provided for each of such values and then enabling the appropriate narrow band in accordance with such coded sequence.

The output from envelope detector 218 is forwarded to alarm-control means, which may take any of the forms disclosed in the aforesaid patent application and in respiration and heartbeat monitors known in the art.

The operation of the embodiment of the present invention shown in FIG. 2 will now be considered. As indicated by arrows 220, antenna element T transmits an original microwave carrier signal to subject 202, some portion of which is back-scattered and received by antenna element M. As indicated by arrows 222, antenna element M, after this received back-scattered portion of the carrier signal has been phase-shifted by the modulation-signal frequency $F_o$, retransmits this phase-shifted back-scattered portion to subject 202, some portion of which is back-scattered and received by antenna element R. However, as indicated by arrows 224, antenna element R also directly receives over a leakage path another back-scattered portion of the originally-transmitted carrier signal from antenna element T that has not been phase shifted by the modulation-signal frequency $F_o$.

The combined darkly-shaded and lightly-shaded areas of subject 202 shown in FIG. 2 represent the interface of the total field pattern of all of linearly-arranged antenna elements T, M and R with subject 202, while the darkly-shaded confined area of subject 202, by itself, represents the interface of the field pattern of only antenna element M with subject 202 (which is the desired target area). Because antenna element M is centrally located between outer-located antenna elements T and R, there will be a large overlap of the field pattern of antenna element M with each of the field patterns of antenna elements T and R. Therefore, antenna element M receives a relatively large back-scatter portion of the original carrier signal transmitted by antenna element T and antenna element R receives a relatively large back-scatter portion of the phase-shifted carrier signal transmitted by antenna element M. However, because outer antenna elements T and R are separated from one another by a larger distance than either one of them is separated from antenna element M, so that there is not much overlap in their field patterns, the back-scatter portion of the original carrier signal transmitted by antenna element T and directly received by antenna element R over the leakage path is relatively small. Further, because of the outer locations of antenna elements T and R, the part of the back-scatter received by antenna element R over the leakage path 224 includes substantially more spurious reflections from outside the desired target area (which includes reflections from objects outside of the patient's thorax in the assumed case) than the part of the back-scatter received by antenna element M over the path 222.

The level of the output of mixer 208, which depends upon the difference between the phase of the received signal applied from antenna element R to its second input and the given phase of the carrier signal applied to its first input, varies in accordance with both (1) phase changes due to changes in effective path lengths caused by reflections from moving objects of each of the phase-modulated first component of the received signal that traveled over path 222 and the leakage second component of the received signal that traveled over path 224, and (2) phase changes due only to the phase modulation of the first component by the $F_o$ modulation signal. Bandpass filter 214, which passes only the phase-modulated first component, blocks all variations in the level of the output of mixer 208 due to the leakage second component. At the output of bandpass filter 241, the amplitude envelope of the $F_o$ modulation signal is indicative of the motion of objects within the target of interest of subject 202 (e.g., the cyclic movement of respiration off patient 100). Envelope detector 218 is then used to derive this amplitude envelope.

While the use of module 106 to house some or all of the elements of FIG. 2 is desirable, it is not essential to the present invention. At the very least, antenna 200 must be situated relatively close to patient 100 to effect irradiation of his thorax. Placing antenna 200, suitable padded, in contact, but not attachment, to patient 100 (as in the case shown in FIG. 1, in which antenna 200 is situated within padded module 106) minimizes spurious relative motion, which can be a problem if bed 102 or the module 106 housing are subject to the slow vibration associated with people walking nearby, the rumbling of machines and pumps, or the shaking of tall buildings by wind gusts. Alternatively, antenna 200 could be placed under the mattress or even on the floor under bed 102, but the closer contact is highly preferable.

If all the elements of FIG. 2 are housed in module 106, the output from enevelope detector 218 may be communicated to alarm-control means situated somewhere else in the patient's room and/or a nurses' station by wire or cable or it may be telemetered by wireless means, such as in the manner disclosed in the aforesaid patient application. Further, one or more of the more terminal processing elements of FIG. 2, such as envelope detector 218, may be situated with and be considered as part of the alarm-control means, rather than being situated in module 106. In this case, the output of the most terminal element still situated in module 106 is communicated to the alarm-control means.

Microwaves penetrate only a few centimeters of body tissue, which is fine for monitoring movement indicative of both the breathing rate and the depth of each breath of the patient. If somewhat deeper penetration is desired, so that movement of and within the heart can be monitored, a somewhat lower carrier-signal frequency may have to be employed. However, such a low carrier-signal frequency lowers to some extent the shielding provided by the patient's body. Further, other forms of radiation, such as ultrasonic radiation, may be substituted for microwave or lower frequency electromagnetic radiation. In such a case, a radiator employing three independent elements, such as three ultrasonic transducers, would be substituted for the three-element antenna 200 employed as a radiator in the above-described illustrative embodiment of the present invention.

Although the circuitry shown in FIG. 2 is particularly suitable for monitoring cyclic movement within the thorax of an individual, it can also be used to monitor any type of movement within any type of tissue of an individual. However, the present invention is not limited to monitoring movement within tissue of an individual. It may also be used to monitor the mechanical movement of life-support equipment, such as a respirator or a heart-lung machine, to control an alarm in response to such equipment failing to operate properly. In fact, the use of the present invention may be extended to such equipment as burglar alarms and the like.

What is claimed is:

1. In apparatus for monitoring movement within certain tissue of an individual; the combination comprising:
   an antenna including three independent elements;
   first means including a source of original carrier signal having a given frequency and phase coupled to a first of said three independent antenna elements for transmitting said original carrier signal into said certain tissue of said individual, whereby some of said transmitted carrier signal is back-scattered and a respective back-scattered portion is received by each of a second and a third of said three independent antenna elements;
   second means including a source of modulation signal having a second frequency and a phase shifter coupled to said second of said three independent antenna elements for phase modulating said back-scattered portion received by said second of said three independent antenna elements in accordance with said modulation signal and retransmitting therefrom said phase-modulated portion back into said certain tissue of said individual, whereby some of said retransmitted phase-modulated portion is back-scattered and received by said third of said three independent antenna elements;
   mixer means coupled to said third of said three independent antenna elements and to said source of original carrier signal for beating both of the back-scattered portions received by said third of said three independent antenna elements against said original carrier signal, whereby said mixer means has an output which includes a component apparatus having said second frequency; and
   third means including bandpass filter means having said mixer-means output applied as an input thereto for passing said mixer-means output component having said second frequency and rejecting all other components of said mixer-means output, whereby said bandpass filter means derives an output signal having an envelope indicative of movement within said certain tissue of said individual.

2. The apparatus defined in claim 1, wherein:
   said three independent elements of said antenna means are linearly arranged with said second of said three independent elements being disposed in between said first and third of said three independent elements so that the field pattern of said second of said three independent elements overlaps to a relatively large extent the respective field patterns of each of said first and third of said three independent elements and the respective field patterns of said first and third of said three independent elements overlap one another to only a relatively small extent at most.

3. The apparatus defined in claim 1, wherein said third means further includes:
   an envelope detector;
   and fourth means for applying the output signal from said bandpass filter means as input thereto.

4. The apparatus defined in claim 3, wherein:
   said fourth means includes a narrow-band amplifier.

5. The apparatus defined in claim 1, wherein said apparatus monitor cyclic movement within the thorax of a patient lying in bed; and wherein said combination further includes:
   a module adjacent said patient housing said antenna means with said three independent elements thereof being adapted to be in padded contact with, but not attached to, the thorax of said patient.

6. The apparatus defined in claim 5, wherein:
said three independent elements of said antenna means are linearly arranged with said second of said three independent elements being disposed in between said first and third of said three independent elements so that the field pattern of said second of said three independent elements overlaps to a relatively large extent the respective field patterns of each of said first and third of said three independent elements and the respective field patterns of said first and third of said three independent elements overlap one another to only a relatively small extent at most.

7. The apparatus defined in claim 6, wherein:
said source of original carrier signal is a microwave oscillator, whereby said first frequency is a microwave frequency.

8. the apparatus defined in claim 6, wherein:
each of said three independent elements of said antenna means comprises a microstrip antenna.

9. The apparatus defined in claim 5, wherein:
said module is a battery-energized module that houses said entire combination.

10. The apparatus defined in claim 1, wherein:
said source of original carrier signal is a microwave oscillator, whereby said first frequency is a microwave frequency.

11. In apparatus for moinitoring movement of or within an object; the combination comprising:
a radiator of a given type of radiation, said radiator including three independent elements;
first means including a source of original carrier signal of said given type of radiation, said original carrier signal having a given frequency and phase coupled to a first of said three independent radiator elements for transmitting said original carrier signal into said object, whereby some of said transmitted carrier signal is back-scattered and a respective back-scattered portion is received by each of a second and a third of said three independent radiator elements;
second means including a source of modulation signal having a second frequency and a phase shifter coupled to said second of said three independent radiator elements for phase modulating said back-scattered portion received by said second of said three independent antenna elements in accordance with said modulation signal and retransmitting therefrom said phase-modulated portion back into said object, whereby some of said retransmitted phase-modulated portion is back-scattered and received by said third of said three independent radiator elements;
mixer means coupled to said third of said three independent radiator elements and to said source of original carrier signal for beating both of the back-scattered portions received by said third of said three independent radiator elements against said original carrier signal, whereby said mixer means has an output which includes a component apparatus having said second frequency; and
third means including bandpass filter means having said mixer-means output applied as an input thereto for passing said mixer-means output component having said second frequency and rejecting all other components of said mixer-means output, whereby said bandpass filter means derives an output signal having an envelope indicative of movement within said object.

* * * * *